United States Patent [19]
Shirai

[11] Patent Number: 5,582,174
[45] Date of Patent: Dec. 10, 1996

[54] ULTRASONIC DIAGNOSTIC SYSTEM

[75] Inventor: Takeshi Shirai, Kawasaki, Japan

[73] Assignee: Fujitsu Limited, Kawasaki, Japan

[21] Appl. No.: 507,973

[22] Filed: Jul. 27, 1995

[30] Foreign Application Priority Data

Dec. 21, 1994 [JP] Japan ..................................... 6-318466

[51] Int. Cl.⁶ ....................................................... A61B 8/00
[52] U.S. Cl. ........................................................ 128/661.01
[58] Field of Search ......................... 128/660.06, 660.07, 128/660.08, 660.09, 660.10, 661.01, 661.08, 661.09, 661.10, 662.03, 662.06

[56] References Cited

U.S. PATENT DOCUMENTS 5,425,370   6/1995   Vilkomerson ...................... 128/662.06

*Primary Examiner*—George Manuel
*Attorney, Agent, or Firm*—Staas & Halsey

[57] ABSTRACT

In an ultrasonic diagnostic system, information as to the inside of the subject is indicated on the basis of a received signal which is obtained through receiving ultrasonic beams reflected within the subject. A difference signal is formed by subtracting a subtraction signal from the received signal, which subtraction signal is generated based on the received signal associated with a scanning line associated with the received signal or a scanning line different from the former scanning line. The difference signal is suitably amplified and analog-to-digital converted.

8 Claims, 3 Drawing Sheets

ULTRASONIC DIAGNOSTIC SYSTEM

BACKGROUND OF THE INVENTION

1. Field of the Invention

The present invention relates to an ultrasonic diagnostic system wherein information as to the inside of a subject is indicated on the basis of received signals which will be obtained through receiving ultrasonic beams or ultrasounds reflected within the subject.

2. Description of the Related Art

There has been used an ultrasonic diagnostic system in which ultrasonic beams are transmitted to the inside of the subject and the human body particularly, the ultrasounds reflected by a tissue in the human body are received in the form of received signals, and an ultrasonic image within the human body based on the received signals is displayed, thereby serving to diagnose diseases of the viscera and the like of the human body. In one aspect of this ultrasonic diagnostic system, or in an optional function of an ultrasonic diagnostic system for displaying a tomographic image (B-mode), there has been used an ultrasonic Doppler diagnostic system in which ultrasounds reflected by blood cells flowing within the human body are received to obtain blood flow information such as velocity, variance, power and the like of the blood flow.

FIG. 3 is a schematic construction view of one example of an ultrasonic diagnostic system.

Since the basic arrangement of the ultrasonic diagnostic system is well known, there will be explained only an arrangement (an ultrasonic Doppler diagnostic system (see U.S. Pat. No. 5,042,491, U.S. Pat. No. 5,215,093)) involved in the present invention in which information representative of a movement within the subject and a blood flow particularly is extracted.

An ultrasonic probe 1 shown in FIG. 3 is constituted of a plurality of ultrasonic transducers 9 toward which pulse signals are each transmitted from a transmitting and receiving circuit 2 in an associated predetermined timing, so that the ultrasonic probe 1 transmits ultrasonic pulse beams to the inside of the subject 30. In this case, for example, a sector scanning is carried out to transmit the ultrasonic pulse beams, for instance, 8 times along each given scan line 31. The ultrasonic pulse beams transmitted to the inside of the subject are reflected by blood cells flowing within the human body and another tissues and received by the plurality of ultrasonic transducers 9 of the ultrasonic probe 1. The received signals received by the ultrasonic transducers 9 are each passed to the transmitting and receiving circuit 2 to be beamformed so as to obtain a received signal carrying information along a predetermined scan line 31. The received signal, which has been subjected to a beamform process, is fed to a quadrature detector 3 to perform a quadrature detection taking as reference signals a sine signal and a cosine signal wherein a center frequency of the ultrasonic wave is given as a reference frequency. The received signal, which has been subjected to a quadrature detection, is fed to an A/D converter 4 to be converted into a digital signal and then passed to an MTI (Moving Target Indication) filter 5. The MTI filter 5 is similar to an MTI filter used in a radar, and usually may be a digital high-pass filter adapted to cut off a low frequency signal, which comprises a delay circuit providing a delay time equivalent to a repeated cycle of the pulse signals and multiplying/ adding device. Such an MTI filter is widely used in the field of the ultrasonic diagnostic system. The MTI filter 5 serves to eliminate a low frequency component of the entered signal, or information as to a motion of a relatively slow speed of tissue within the subject, and extract a signal carrying information (blood flow information) as to a relatively high speed of blood flow.

The signal outputted from the MTI filter 5 is fed to a velocity operating circuit 6 to evaluate a blood flow velocity. Information representative of the blood flow velocity thus obtained is passed to a scan converter 7 to be converted into an indication signal. Such an indication signal is superposed on, for example, a B-mode image produced by a B-mode image producing circuit (not illustrated) and then displayed on a display screen of a CRT 8 with a color for example.

As mentioned above, the ultrasonic received signal includes a component (referred to as "clutter information" hereinafter) obtained through receiving the ultrasonic beams reflected by tissues and a component (blood information) obtained through receiving the ultrasonic beams reflected by blood cells. Usually, the clutter information has a power (the order of 20dB–50dB) which is extremely larger than that of the blood information. Consequently, assuming that the A/D converter 4 produces, for example, 10 bits of digital signals, the blood information will be represented by 2 or 3 bits of 10 bits. The digital signals outputted from the A/D converter 4 is fed to the MTI filter 5 to eliminate the clutter information, so that the blood information represented by 2 or 3 bits is extracted. This involves low resolution of blood information. Therefore, it will bring about a problem such that a precision of the velocity of the blood flow evaluated in the velocity operating circuit 6 is very bad. The bad precision of the velocity of the blood flow causes such a situation that particularly in peripheral blood vessels or the like, which are small in a received signal level, the blood flow is not extracted in spite of the presence of the blood flow. Thus, it happens that the blood flow is not displayed on the CRT 8.

In order to enhance the precision, it is considered that a bit length in the A/D converter 4 is increased. This will involve, however, an enlargement of the scale of the A/D converter 4, the succeeding MTI filter 5, the velocity operating circuit 6 and the like. Thus, it brings about such a problem that the system is obliged to increase remarkably the cost for fabrication.

In view of the foregoing, it is an object of the present invention to provide an ultrasonic diagnostic system capable of extracting information as to motion within the subject, without enlarging a bit length of the A/D conversion.

SUMMARY OF THE INVENTION

To attain the above-mentioned object of the invention, according to the present invention, there is provided an ultrasonic diagnostic system comprising:

(1) ultrasonic receiving means for receiving ultrasonic beams reflected by points on each of a plurality of scanning lines extending within a subject to form received signals corresponding to the associated scanning line;

(2) subtraction signal generating means for generating a predetermined subtraction signal;

(3) difference signal generating means for performing arithmetic on a difference between the received signal and the subtraction signal to generate a difference signal;

(4) A/D converting means for performing an A/D conversion of the difference signal to form a digital difference signal;

(5) movement information calculating means for calculating information representative of a movement within the subject on the basis of the digital difference signal; and (6) display means for displaying an image based on the information calculated by said movement information calculating means.

It is preferable that said difference signal generating means performs arithmetic on a difference between the received signal after detection and the subtraction signal.

It is acceptable that said difference signal generating means produces the subtraction signal, which is used to perform arithmetic on a difference between it and the received signal associated with a predetermined scanning line, on the basis of the received signal associated with the predetermined scanning line, or on the basis of the received signal associated with a scanning line different from the predetermined scanning line.

Further, it is acceptable that said difference signal generating means produces the subtraction signals, which are each used to perform arithmetic on a difference between it and the received signal associated with each of the plurality of scanning lines, on the basis of a plurality of received signals which are obtained through a plurality of number of times of receiving of the ultrasonic beams for each scan line, or on the basis of a single received signal which is obtained through receiving once the ultrasonic beam for each scan line.

To eliminate clutter information, as mentioned above, there is used, for example, an MTI filter to eliminate the low frequency signal component. When a difference signal is evaluated through subtracting a predetermined subtraction signal from a received signal, the difference signal is equivalent to a signal resulting through elimination of a DC component of the received signal. Such a DC component of the received signal is a component which ought to be eliminated when the clutter information is eliminated by the MTI filter and the like. Consequently, performing arithmetic based on the difference signal makes no problem. Further, it is noted that a major part of clutter information is included in the DC component. Hence, the difference signal may include blood flow information with a higher concentration comparing with the received signal before elimination of the DC component, thereby extremely enhancing the intensity ratio of the blood flow information to the clutter information. Thus, performing an A/D conversion of the difference signal with an amplification until a suitable signal level for the A/D conversion may enhance resolution of the blood flow information. Accordingly, it is possible to detect the blood flow information such as blood flow velocity with high precision.

While the difference signal generating means may perform arithmetic on a difference between the received signal before the detection and the associated subtraction signal, the received signal after the detection is more suitable for the arithmetic operation. Therefore, providing a difference signal generating means, which is adapted to perform arithmetic on a difference between the received signal after the detection and the associated subtraction signal, makes an arrangement of the difference signal generating means simplified.

Further, in a case where the difference signal generating means produces the subtraction signal, which is used to perform arithmetic on a difference between it and the received signal associated with a predetermined scanning line, on the basis of the received signal associated with the predetermined scanning line, it is possible to generate a difference signal from which the DC component has been eliminated with greater accuracy. However, in this case, there is a need to perform an ultrasonic beam transmission and receiving operation once too many to generate the subtraction signal. This involves a fear such that a frame rate is deteriorated.

On the contrary, in a case where the difference signal generating means produces the subtraction signal, which is used to perform arithmetic on a difference between it and the received signal associated with a predetermined scanning line, on the basis of the received signal associated with a scanning line different from the predetermined scanning line, for example, typically, the adjacent scanning line, it is possible to avoid the deterioration of the frame rate, but there is a possibility that the DC component remains a little bit. However, a remainder of the DC component itself involves no problem as far as it has no effect on resolution of an A/D conversion, since the remaining DC component is removed in the succeeding process in which the clutter component is eliminated.

In producing the subtraction signals, which are each used to perform arithmetic on a difference between it and the received signal associated with each of the plurality of scanning lines, it is acceptable that those subtraction signals are each produced on the basis of a plurality of received signals which are obtained through a plurality of number of times of receiving of the ultrasonic beams for each scan line, or on the basis of a single received signal which is obtained through receiving once the ultrasonic beam for each scan line. Producing each of the subtraction signals on the basis of a plurality of received signals makes it possible to produce the subtraction signal involving less noises or the like. On the other hand, in a case where the subtraction signal, which is used to perform arithmetic on a difference between it and the received signal associated with a predetermined scanning line, is produced on the basis of the received signal associated with the predetermined scanning line, producing the subtraction signal on the basis of a plurality of received signals may involve the corresponding deterioration of frame rate. Consequently, as to the matter such that the subtraction signal is produced on the basis of how many received signals, it is selected taking into account a frame rate, a necessary precision and the like.

DESCRIPTION OF THE PREFERRED EMBODIMENTS

Hereinafter, there will be described embodiments of the present invention.

Figure 1:
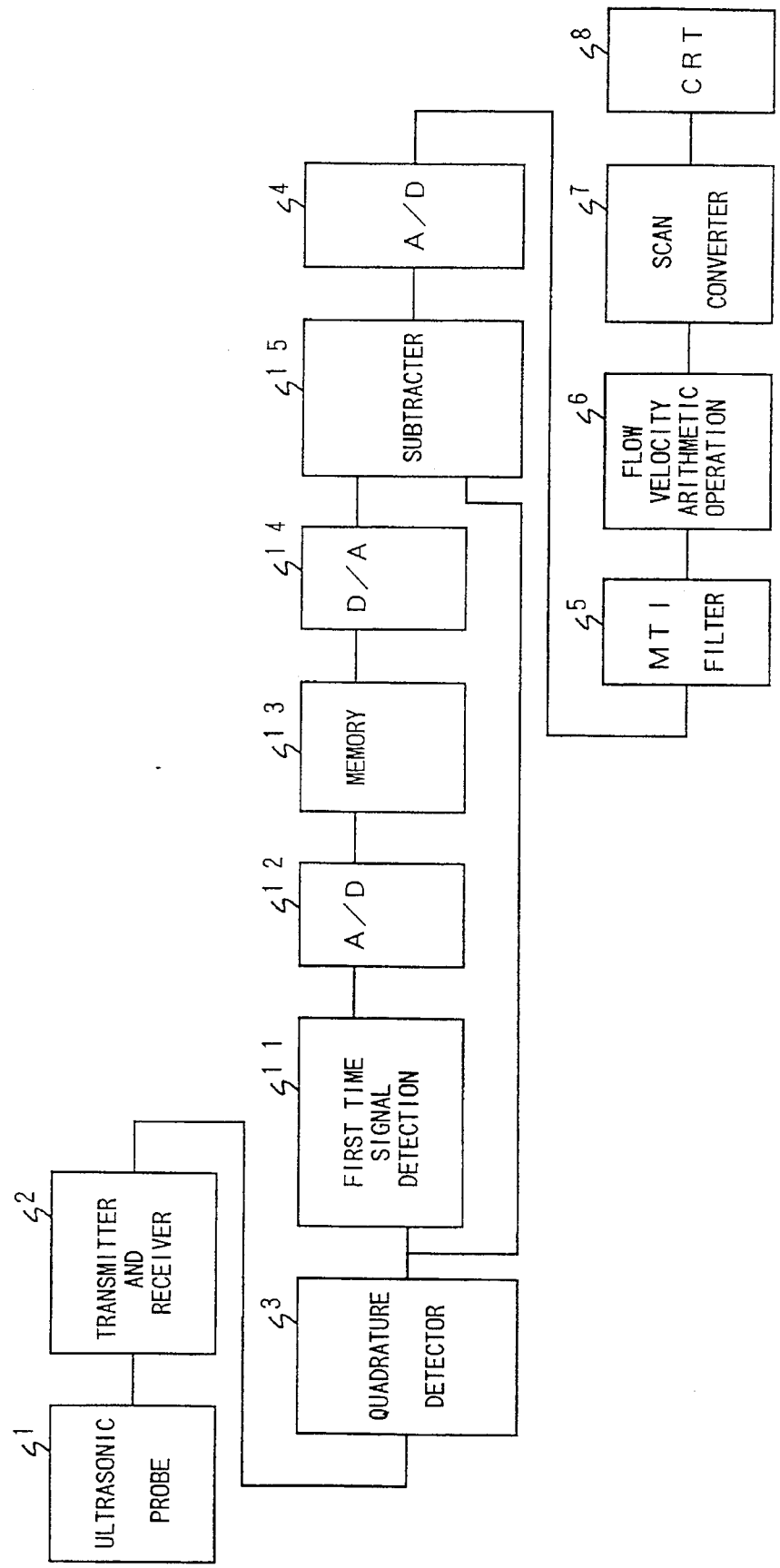
FIG. 1 is a partial block diagram of an ultrasonic diagnostic system according to a first embodiment of the present invention.
Figure 3:
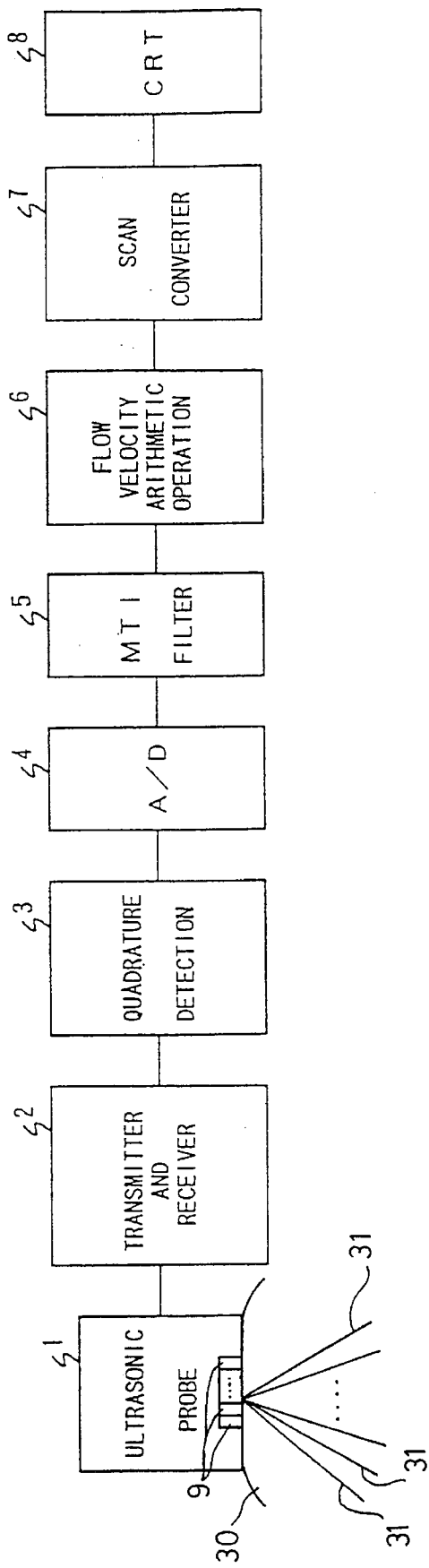
FIG. 3 is a schematic construction view of one example of an ultrasonic diagnostic system.

FIG. 1 is a partial block diagram of an ultrasonic diagnostic system according to a first embodiment of the present invention. In FIG. 1, the same constituents of the ultrasonic diagnostic system as that shown in FIG. 3 are denoted by the same reference numbers as those in FIG. 3 and the redundant description will be omitted.

In the ultrasonic diagnostic system according to the present embodiment, there is repeated such a sequence that an operation of transmission and reception of the ultrasonic beams is performed eight times with respect to a certain scan line, and then the same operation is performed eight times with respect to the adjacent scan line.

The received signal outputted from the quadrature detector 3, which has been subjected to a quadrature detection process, is supplied to a first time signal detection circuit 11 and a subtracter 15. In the first time signal detection circuit 11, it is identified whether the received signal is a received signal (referred to as "the first time received signal" hereinafter) which is obtained through an operation of transmission and reception of the ultrasonic beam for the first time among eight times of operation of transmission and reception of the ultrasonic beams carried out with respect to the same scan line, or a received signal which is obtained through an operation of transmission and reception of the ultrasonic beam for the second time et seqq., and in case of the first time, the first time received signal is passed to an A/D converter 12. The A/D converter 12 is different from the claimed terminology "A/D converting means", but is equivalent to an example of the claimed terminology "subtraction signal generating means" using together with the first time signal detection circuit 11, a memory 13 and a D/A converter 14 which will be described later. The first time received signal in a digital form outputted from the A/D converter 12 is stored in the memory 13. This first time received signal in a digital form is equivalent to an example of the claimed terminology "subtraction signal".

The first time received signal in a digital form or the subtraction signal is read out from the memory 13, converted into an analog subtraction signal by the D/A converter 14 and supplied to a subtracter 15 under a timing control such that the received signal involved in the same depth on the same scanning line and the subtraction signal are simultaneously supplied to the subtracter 15 in synchronism with such a timing that the received signals obtained through operation of transmission and reception of the ultrasonic beams for the second time et seqq. along the same scanning line are detected by the quadrature detector 3 and then supplied to the subtracter 15. The subtracter 15 is equivalent to the claimed terminology "difference signal generating means". In the subtracter 15, the subtraction signal is subtracted from the received signal involved in the same depth point on the same scanning line to evaluate a difference signal. The difference signal is amplified suitably in accordance with necessity and then fed to the A/D converter 4 so as to be converted into a difference signal in a digital form. The difference signal in a digital form is passed, as shown in FIG. 3, to the MTI filter 5 so that a clutter component is eliminated. An output of the MTI filter 5 is fed to the velocity operating circuit 6 to evaluate a blood flow velocity. An output of the velocity operating circuit 6 is passed to the scan converter 7 so as to be converted into an indication signal. Thus, the blood flow velocity is displayed on a display screen of a CRT 8 with a color for example. Incidentally, in the present embodiment, the A/D converter 4 is equivalent to the claimed terminology "A/D converting means".

Figure 2:
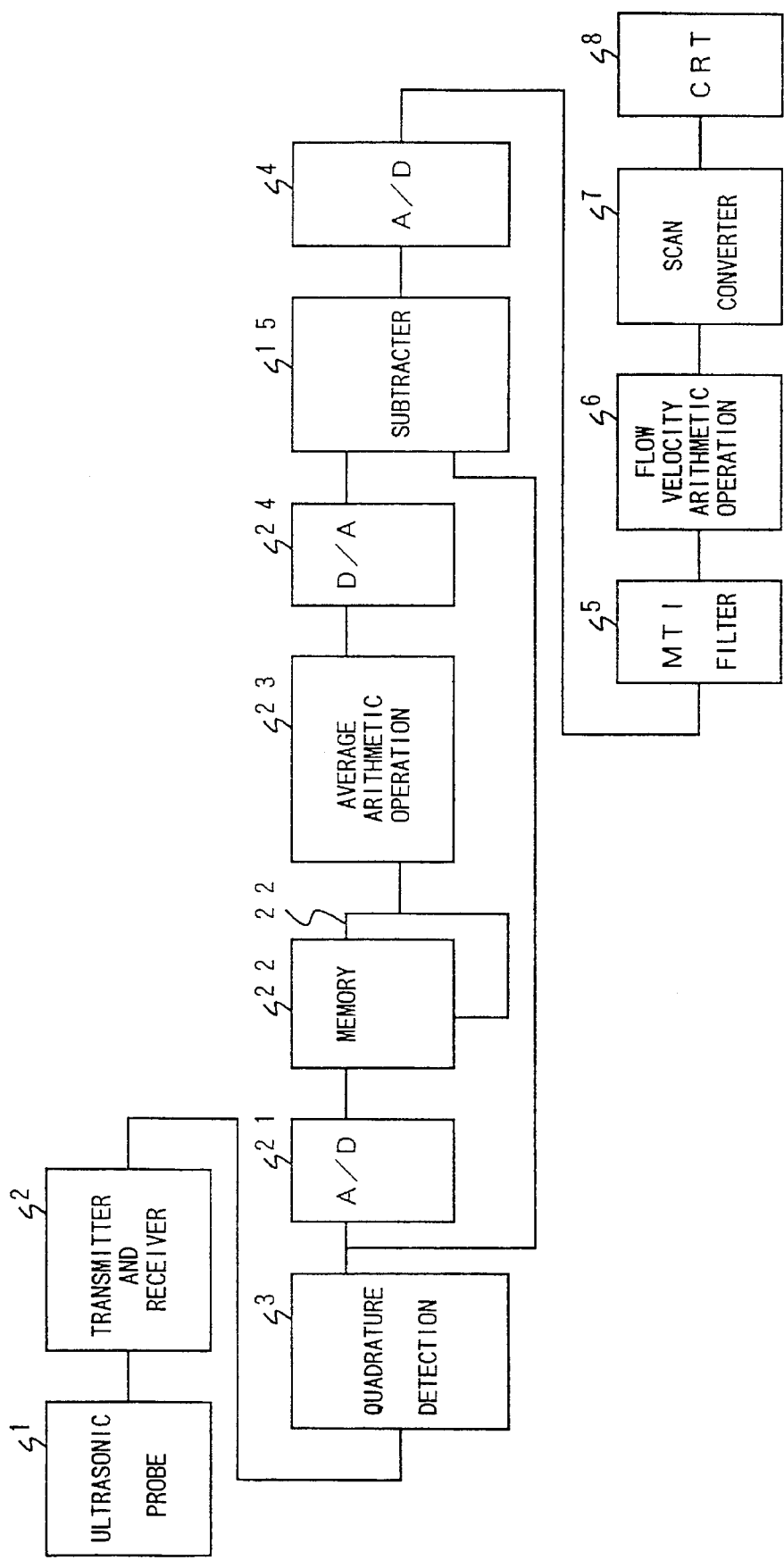
FIG. 2 is a partial block diagram of an ultrasonic diagnostic system according to a second embodiment of the present invention.

FIG. 2 is a partial block diagram of an ultrasonic diagnostic system according to a second embodiment of the present invention. Also in FIG. 2, in a similar fashion to that of FIG. 1, the same constituents of the ultrasonic diagnostic system as that shown in FIG. 3 are omitted, and the same parts are denoted by the same reference numbers as those in FIG. 3 and the redundant description will be omitted.

The received signal outputted from the quadrature detector 3, which has been subjected to a quadrature detection process, is supplied to an A/D converter 21 and the subtracter 15. In the A/D converter 21, the received signal as an input is converted into a received signal in a digital form. The digital received signal is stored in a memory 22. Now let us consider such a state that eight times of operation of transmission and reception of the ultrasonic beam along a certain scanning line is over and an operation of transmission and reception of the ultrasonic beam along the adjacent scanning line is initiated. At that time, the memory 22 has stored eight digital received signals obtained through performing the associated operation of transmission and reception of the ultrasonic beam immediately before the operation of transmission and reception of the ultrasonic beam along the adjacent scanning line.

When the quadrature detector 3 detects the received signals associated with the adjacent scanning line and outputs the received signals thus detected, these detected received signals are passed, in a similar fashion to that of the above, to the A/D converter 21 and the subtracter 15. In synchronism with this operation, eight digital received signals associated with the preceding scanning line are read out from the memory 22 so that an average operating circuit 23 evaluates an average for each depth on the scanning line, thereby generating a subtraction signal representative of the average of the eight digital received signals. The subtraction signal thus generated is converted by a D/A converter 24 into an analog subtraction signal and passed to the subtracter 15. In the subtracter 15, the subtraction signal is subtracted from the received signal involved in the same depth point on the same scanning line to evaluate a difference signal. As mentioned above, the difference signal is obtained through subtracting an average of the eight received signals associated with the preceding scanning line from the received signals associated with a certain scanning line. This difference signal is amplified suitably in accordance with necessity and then fed to the A/D converter 4 so as to be converted into a difference signal in a digital form. The difference signal in a digital form is passed, as shown in FIG. 3, to the MTI filter 5 so that a clutter component is eliminated. An output of the MTI filter 5 is fed to the velocity operating circuit 6 to evaluate a blood flow velocity. An output of the velocity operating circuit 6 is passed to the scan converter 7 so as to be converted into an indication signal. Thus, the blood flow velocity is displayed on a display screen of a CRT 8 with a color for example.

Incidentally, in the second embodiment, a combination of the A/D converter 21, the memory 22, the average operating circuit 23 and the D/A converter 24 is equivalent to an example of the claimed terminology "subtraction signal generating means".

In accordance with the first embodiment wherein the received signal associated with the same scanning line is adopted as the subtraction signal, the subtraction signal is generated on the basis of a single received signal only, whereas in accordance with the second embodiment wherein the received signals associated with the adjacent scanning line are adopted as the subtraction signal, the subtraction signal is generated on the basis of a plurality of received signals. It is acceptable, however, that even in a case where the received signal associated with the same scanning line is adopted as the subtraction signal, the subtraction signal is generated on the basis of a plurality of received signals, or even in a case where the received signal associated with the different scanning line is adopted as the subtraction signal, the subtraction signal is generated on the basis of a single received signals only.

As described above, in the ultrasonic diagnostic system according to the present invention, a difference signal is obtained through performing arithmetic on a difference between the received signal and the subtraction signal. Thus, according to the present invention, it is possible to enhance resolution of information as to motion within the subject and thus detect information as to the motion with higher precision.

The present invention is not limited to the particular embodiments described above. Various changes and modifications may be made within the spirit and scope of the invention.

What is claimed is:

1. An ultrasonic diagnostic system comprising:
    ultrasonic receiving means for receiving ultrasonic beams reflected by points on each of a plurality of scanning lines extending within a subject to form received signals corresponding to the associated scanning line;
    subtraction signal generating means for generating a predetermined subtraction signal;
    difference signal generating means for performing arithmetic on a difference between the received signal and the subtraction signal to generate a difference signal,
        wherein said difference signal generating means performs arithmetic on a difference between the received signal after detection and the subtraction signal, and
        wherein said difference signal generating means produces the subtraction signal, which is used to perform arithmetic on a difference between it and the received signal associated with a predetermined scanning line, on the basis of the received signal associated with the predetermined scanning line;
    A/D converting means for performing an A/D conversion of the difference signal to form a digital difference signal;
    movement information calculating means for calculating information representative of a movement within the subject on the basis of the digital difference signal; and
    display means for displaying an image based on the information calculated by said movement information calculating means.

2. A system according to claim 1, wherein said difference signal generating means produces the subtraction signals, which are each used to perform arithmetic on a difference between it and the received signal associated with each of the plurality of scanning lines, on the basis of a plurality of received signals which are obtained through a plurality of number of times of receiving of the ultrasonic beams for each scan line.

3. A system according to claim 1, wherein said difference signal generating means produces the subtraction signals, which are each used to perform arithmetic on a difference between it and the received signal associated with each of the plurality of scanning lines, on the basis of a single received signal which is obtained through receiving once the ultrasonic beam for each scan line.

4. An ultrasonic diagnostic system comprising:
    ultrasonic receiving means for receiving ultrasonic beams reflected by points on each of a plurality of scanning lines extending within a subject to form received signals corresponding to the associated scanning line;
    subtraction signal generating means for generating a predetermined subtraction signal;
    difference signal generating means for performing arithmetic on a difference between the received signal and the subtraction signal to generate a difference signal,
        wherein said difference signal generating means produces the subtraction signal, which is used to perform arithmetic on a difference between it and the received signal associated with a predetermined scanning line, on the basis of the received signal associated with a scanning line different from the predetermined scanning line;
    A/D converting means for performing an A/D conversion of the difference signal to form a digital difference signal;
    movement information calculating means for calculating information representative of a movement within the subject on the basis of the digital difference signal; and
    display means for displaying an image based on the information calculated by said movement information calculating means.

5. An ultrasonic diagnostic system comprising:
    ultrasonic receiving means for receiving ultrasonic beams reflected by points on each of a plurality of scanning lines extending within a subject to form received signals corresponding to the associated scanning line;
    subtraction signal generating means for generating a predetermined subtraction signal;
    difference signal generating means for performing arithmetic on a difference between the received signal and the subtraction signal to generate a difference signal,
        wherein said difference signal generating means performs arithmetic on a difference between the received signal after detection and the subtraction signal, and
        wherein said difference signal generating means produces the subtraction signal, which is used to perform arithmetic on a difference between it and the received signal associated with a predetermined scanning line, on the basis of the received signal associated with a scanning line different from the predetermined scanning line;
    A/D converting means for performing an A/D conversion of the difference signal to form a digital difference signal;
    movement information calculating means for calculating information representative of a movement within the subject on the basis of the digital difference signal; and
    display means for displaying an image based on the information calculated by said movement information calculating means.

6. An ultrasonic diagnostic system comprising:
    ultrasonic receiving means for receiving ultrasonic beams reflected by points on each of a plurality of scanning lines extending within a subject to form received signals corresponding to the associated scanning line;
    subtraction signal generating means for generating a predetermined subtraction signal;
    difference signal generating means for performing arithmetic on a difference between the received signal and the subtraction signal to generate a difference signal,
        wherein said difference signal generating means produces the subtraction signals, which are each used to perform arithmetic on a difference between it and the received signal associated with each of the plurality of scanning lines, on the basis of a plurality of received signals which are obtained through a plurality of number of times of receiving of the ultrasonic beams for each scan line;
    A/D converting means for performing an A/D conversion of the difference signal to form a digital difference signal;

movement information calculating means for calculating information representative of a movement within the subject on the basis of the digital difference signal; and display means for displaying an image based on the information calculated by said movement information calculating means.

7. An ultrasonic diagnostic system comprising:

ultrasonic receiving means for receiving ultrasonic beams reflected by points on each of a plurality of scanning lines extending within a subject to form received signals corresponding to the associated scanning line;

subtraction signal generating means for generating a predetermined subtraction signal;

difference signal generating means for performing arithmetic on a difference between the received signal and the subtraction signal to generate a difference signal, wherein said difference signal generating means performs arithmetic on a difference between the received signal after detection and the subtraction signal, and wherein said difference signal generating means produces the subtraction signals, which are each used to perform arithmetic on a difference between it and the received signal associated with each of the plurality of scanning lines, on the basis of a plurality of received signals which are obtained through a plurality of number of times of receiving of the ultrasonic beams for each scan line;

A/D converting means for performing an A/D conversion of the difference signal to form a digital difference signal;

movement information calculating means for calculating information representative of a movement within the subject on the basis of the digital difference signal; and display means for displaying an image based on the information calculated by said movement information calculating means.

8. An ultrasonic diagnostic system comprising:

ultrasonic receiving means for receiving ultrasonic beams reflected by points on each of a plurality of scanning lines extending within a subject to form received signals corresponding to the associated scanning line;

subtraction signal generating means for generating a predetermined subtraction signal;

difference signal generating means for performing arithmetic on a difference between the received signal and the subtraction signal to generate a difference signal, wherein said difference signal generating means produces the subtraction signal, which is used to perform arithmetic on a difference between it and the received signal associated with a predetermined scanning line, on the basis of the received signal associated with the predetermined scanning line, and wherein said difference signal generating means produces the subtraction signals, which are each used to perform arithmetic on a difference between it and the received signal associated with each of the plurality of scanning lines, on the basis of a plurality of received signals which are obtained through a plurality of number of times of receiving of the ultrasonic beams for each scan line;

A/D converting means for performing an A/D conversion of the difference signal to form a digital difference signal;

movement information calculating means for calculating information representative of a movement within the subject on the basis of the digital difference signal; and display means for displaying an image based on the information calculated by said movement information calculating means.

\* \* \* \* \*